United States Patent [19]

Savu

[11] Patent Number: 4,739,112
[45] Date of Patent: Apr. 19, 1988

[54] PERFLUOROPOLYCYCLOALKANES

[75] Inventor: Patricia M. Savu, Maplewood, Minn.

[73] Assignee: Minnesota Mining and Manufacturing Company, St. Paul, Minn.

[21] Appl. No.: 697,508

[22] Filed: Feb. 1, 1985

[51] Int. Cl.$^4$ .................... C07C 69/52; C07C 51/58; C07C 19/08; C09K 5/00

[52] U.S. Cl. .................... 560/220; 252/78.1; 260/544 F; 568/819; 570/130

[58] Field of Search ............... 560/116, 220; 570/130, 570/131; 568/819; 260/544 F; 252/78.1

[56] References Cited

U.S. PATENT DOCUMENTS

| | | | |
|---|---|---|---|
| 2,717,871 | 9/1955 | Scholberg et al. | 204/59 R |
| 3,028,321 | 4/1962 | Danielson et al. | 204/59 |
| 3,461,155 | 8/1969 | Rice | 560/145 |
| 3,480,667 | 11/1969 | Siegart et al. | 549/246 |
| 3,600,433 | 8/1971 | Holland et al. | 560/125 |
| 3,699,156 | 10/1972 | Holland et al. | 526/245 |
| 3,775,489 | 4/1971 | Margrave et al. | 570/130 |
| 3,849,504 | 11/1974 | Mitsch | 568/615 |

OTHER PUBLICATIONS

Harris, J. F., Jr., J. Org. Chem., vol. 30, pp. 2182–2190, 1965.
J. Org. Chem., vol. 35, No. 8, p. 2816, 1970.
Danielson, Kirk–Othmer Encyclopedia of Chemical Technology, 3rd edition, vol. 10, p. 874, 1980.

*Primary Examiner*—Michael L. Shippen
*Assistant Examiner*—Patricia M. Scott
*Attorney, Agent, or Firm*—D. M. Sell; J. A. Smith; C. Truesdale

[57] ABSTRACT

Perfluoropolycycloalkanes are provided. These perfluoropolycycloalkanes are ring assemblies having (a) at least two perfluorinated cyclohexane rings, (b) at least two perfluorinated fused ring systems, or (c) combinations of at least one perfluorinated cyclohexane ring with at least one perfluorinated fused ring system, each perfluorinated ring or fused ring system being directly joined to another perfluorinated ring or ring system by a single bond and the ring assemblies having a total of at least 13 carbon atoms.

5 Claims, No Drawings

PERFLUOROPOLYCYCLOALKANES

This invention relates to perfluoropolycycloalkane compositions.

Various perfluorochemical compounds and processes for preparing such compounds are known in the art. The synthesis of long chain fluoroalkanes by photolysis of open chain perfluoroacyl fluorides has been reported (J. Org. Chem. 30, 2182 (1965). The synthesis of high molecular weight perfluoropolyethers by photolysis of ether-containing diacyl fluorides is also known (J. Org. Chem. 35, 2816 (1970) and U.S. Pat. No. 3,849,504). U.S. Pat. No. 3,480,667 discloses fluorination of certain aromatic and polynuclear compounds by using an alkali metal fluoride catalyst. U.S. Pat. No. 3,600,433 discloses perfluorinated cyclohexane having a perfluoroalkyl side chain of 2 to 10 carbon atoms prepared by electrolytic fluorination. U.S. Pat. No. 3,699,156 discloses perfluorocyclohexane carbonyl fluoride and perfluoro(alkyl cyclohexane) carbonyl fluorides, prepared by electrolytic fluorination. U.S. Pat. No. 3,775,489 discloses polynuclear perfluoroaromatic compounds prepared by direct fluorination with controlled flow rate.

The present invention provides fluorochemical compositions comprising compounds in the form of perfluoropolycycloalkane ring assemblies having (a) at least two perfluorinated cyclohexane rings, (b) at least two perfluorinated fused ring systems, or (c) a combination of at least one perfluorinated cyclohexane ring with at least one perfluorinated fused ring system, each perfluorinated ring or ring system being directly joined to another perfluorinated ring or fused ring system by a single bond and the ring assembly having a total of at least 13 carbon atoms.

Examples of said compounds are

The perfluoropolycycloalkanes of this invention are, especially in the inert, non-functional form, nonflammable, thermally stable, and resistant to oxidation, properties which make them particularly useful as high performance fluids for use in high temperature environments, e.g., as inert fluids, heat transfer fluids, and pump fluids. In the reactive, functional form, these perfluoropolycycloalkanes are useful as fluorochemical reagents, monomers and intermediates, for example, hydroxyl group-containing compounds can be used to prepare acrylate monomers or urethane derivatives.

The perfluoropolycycloalkane ring assemblies of the present invention can be prepared by the photodimerization of perfluorocycloalkane carbonyl fluoride compounds, such as 1,3-perfluorocyclohexane dicarbonyl fluoride, and 1,5-perfluoro(decahydronaphthalene) dicarbonyl fluoride.

The perfluorocycloalkane carbonyl fluoride precursors used in the photodimerization, i.e., photolysis, process can be prepared by electrochemical fluorination of the appropriate cyclic hydrocarbon starting materials in liquid hydrogen fluoride following the procedures described in U.S. Pat. No. 2,717,871, which description is incorporated by reference herein. The crude acid fluoride products can be treated with sodium fluoride, filtered, and distilled to obtain the purified perfluorocycloalkane carbonyl fluorides. The purified perfluorocycloalkane carbonyl fluorides thus obtained can be photolyzed using a ultraviolet light source, for example a 450-watt medium pressure mercury vapor lamp, to cause bond cleavage between the carbonyl fluoride carbon atom and the carbon ring atom to which it is bonded, followed by coupling of the perfluorocycloalkane radicals to yield the perfluoropolycycloalkane compounds of this invention.

The product of the photolysis reaction is generally a

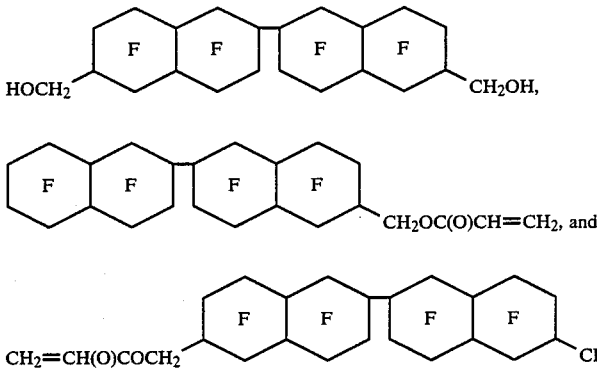

As used herein, the term "ring assembly" refers to at least two ring systems or fused ring systems joined by single bonds.

A preferred class of these perfluoropolycycloalkanes are those represented by the general formula

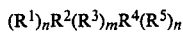

where $R^1$ and $R^5$ are ring substituents selected from —F, —COF and derivatives thereof, perfluoroalkyl groups having, for example, 1 to 4 carbon atoms, and perfluorocycloalkyl groups having, for example, 4 to 14 carbon atoms; $R^2$, $R^3$ and $R^4$ are, independently, perfluorocycloalkane rings or fused ring systems; n is 1 or 2; and m is 0 or a number less than 5.

mixture of the perfluorocycloalkane products which make up a major amount of the composition, generally at least 50 weight percent and usually up to 70 weight percent. In addition, small amounts of by-products, such as ring-contracted, ring-opened, and ring-expanded compounds, can be present in the mixtures or reaction products as a result of the reaction conditions involved in their preparation. The presence of such by-products, in amounts, for example, up to 30 weight percent of the reaction product, but generally less than 15 weight percent of the reaction product, generally does not affect the usefulness of the perfluoropolycycloalkane compounds in admixture therewith.

A representative scheme for the fluorination and photocoupling processes is as follows:

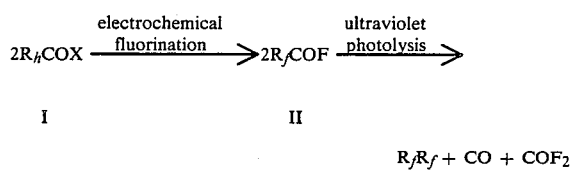

$$R_fR_f + CO + COF_2$$

III where $R_h$ is a cycloaliphatic radical derived from cyclohexane or decahydronaphthalene or aromatic radical, X is Cl, F, or OCH$_3$, and $R_f$ is a perfluorocycloalkane radical. It should be noted that $R_fCOF$, product II, usually contains some $R_fF$ from cleavage during the electrochemical fluorination. $R_fF$ compounds are generally not separated and thus are present during photolysis and in the final photolysis products. Representative cyclic hydrocarbon (aromatic) starting materials (I), fluorinated cyclic acid fluorides (II), and the final perfluorocyclic photolysis products (III) are shown in Table 1.

A wide variety of perfluorocyclic photolysis products (III) can be made, especially from the photolysis of diacid fluorides or mixtures containing diacid fluorides. For example, in Table 1

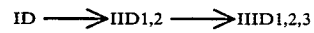

and

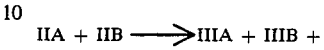

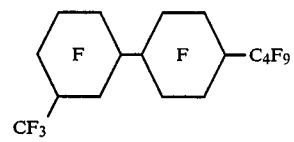

In the structural formulas, the "F" within a ring structure conventionally denotes that the ring is perfluoro, i.e., all the ring carbon atoms are bonded to fluorine atoms and also may be bonded to substituents, e.g. CF$_3$ or C$_4$F$_9$.

TABLE 1

| CYCLIC HYDROCARBON STARTING MATERIALS (I) | FLUORINATED CYCLIC ACID FLUORIDES (II) | PERFLUOROPOLYCYCLOALKANE PHOTOLYSIS PRODUCTS(S) (III) |
|---|---|---|
| 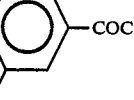<br>IA | 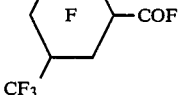<br>IIA | 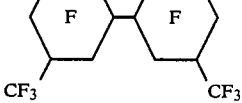<br>IIIA |
| 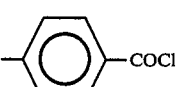<br>IB | 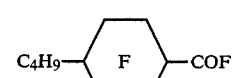<br>IIB | 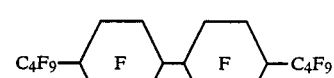<br>IIIB |
| <br>IC | 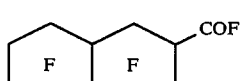<br>IIC | 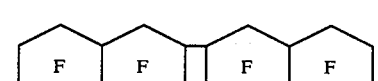<br>IIIC1 |
| | <br>IIA | IIIA, IIICl, 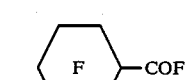<br>IIIC2 |
| | 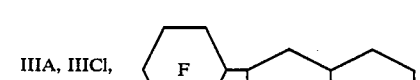<br>IIC | |
| 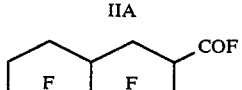<br>ID | 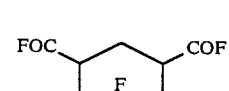<br>IIDI | 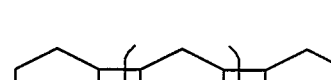<br>m = 0 IIID1<br>m = 1 IIID2<br>m = 2 IIID3 |

TABLE 1-continued

| CYCLIC HYDROCARBON STARTING MATERIALS (I) | FLUORINATED CYCLIC ACID FLUORIDES (II) | PERFLUOROPOLYCYCLOALKANE PHOTOLYSIS PRODUCTS(S) (III) |
|---|---|---|
| | IID2 | IIID4 |
| IE | IIE1 | IIIE $R^1 = F, COF$ |
| | IIE2 | |
| IF | IIF1 | IIIF $R^1 = F, COF$ |
| | IIF2 | |

In addition to the major perfluorocyclic coupled products shown in Table 1, Column III, minor amounts of oxygen-containing products are also formed in the photolysis reaction. These by-products which do not detract from the usefulness of the composition may be present in amounts of up to 10 weight percent and are believed to form as follows In the photolysis step, $R_f$ radicals can form from $R_fCOF$, which, in addition to coupling to form the major products $R_fR_f$, can also react to a limited extent at the oxygen atom of the —COF groups to yield minor amounts of ether-containing products, e.g. $(R_f)_2CFOR_f$, (IV), as shown below.

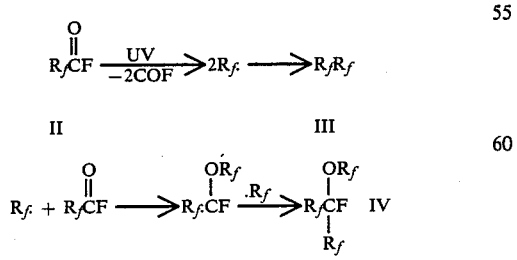

For example, a type IV ether product (IVA) is formed along with the major coupled product IIIA on photolysis of IIA.

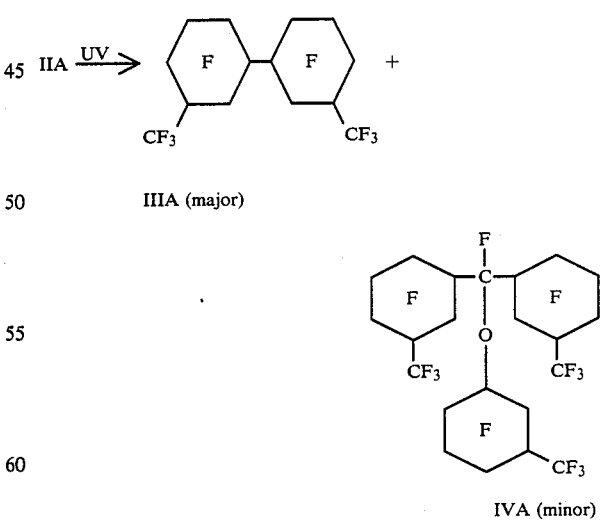

IIIA (major)

IVA (minor)

In the photolytic coupling process used in this invention, various types of photoreactors can be employed. These include simple immersion reactors and recycle reactors. In the simple immersion reactor, the ultraviolet light source, e.g. a 450-watt medium pressure mercury lamp, generally located inside a water-cooled quartz sleeve, is placed in the perfluorocycloalkane carbonyl fluoride solution in a reaction vessel, and photolysis is carried out for the desired period (see Harris, J. F., Jr. J. Org. Chem. Vol. 30, pp. 2182–2190, 1965).

A recycle reactor, such as that disclosed by Mitsch (J. Org. Chem., Vol. 35, No. 8, pg. 2816, 1970), is generally preferred for the photolytic coupling process since it is more efficient than immersion reactors.

The recycle reactor for the photolytic coupling process consists of refluxing a fluorochemical acid fluoride under a dry nitrogen atmosphere, with or without a suitable codistilling solvent, into the photoreactor zone where the liquid phase is photolyzed and then returned to the flask. During the course of the reaction, the higher molecular weight acid fluoride produced, hereinafter referred to as "coupled ring assembly product," is returned to the flask and remains therein while the lower boiling starting acid fluoride continues to reflux and is recycled to the photolysis chamber. In general, the residence time is determined empirically and the return tube leading from the photolysis chamber to a Vigreux column is made with appropriate dimensions to accomplish the desired residence time. It is necessary to gradually increase the temperature of the flask in order to ensure vaporization of the progressively decreasing amount of starting acid fluoride. Thus, the extent of reaction can be followed by monitoring the pot temperature or more exactly by vapor phase chromatographic analysis of aliquots withdrawn from the flask. Low boiling and gaseous by-products of the reaction, primarily oxalyl fluoride and minor amounts of carbonyl fluoride and carbon monoxide, are allowed to escape through the top of the condenser.

After the desired photolysis period (typically 16–30 hours), the crude reaction product mixture from the photoreactor is fractionally distilled. The difference in boiling points between a monoacid fluoride starting material and the coupled product is generally at least about 90° C., facilitating separation by distillation. For example, perfluoro-3-methylcyclohexane carbonyl fluoride (IIA) boils at 100° C., while the coupled product, perfluoro-3,3'-dimethylbicyclohexane (IIIA) boils in the range of 205°–215° C.

Perfluorocycloalkane coupled ring assembly products, prepared from monoacid fluorides, may be used directly, for example, as inert fluids and heat transfer fluids for vapor phase soldering. (See Danielson, Kirk-Othmer Encyclopedia of Chemical Technology, 3rd Edition, Vol. 10, page 874, 1980).

Coupled ring assembly products prepared from diacid fluorides may contain residual carbonyl fluoride groups. These functional compounds can be stabilized by decarbonylation by treatment with cobalt trifluoride, e.g., $R_fR_f'COF + 2CoF_3 \rightarrow R_fR_f'F + CoF_2 + COF_2$. The stabilized product is then suitable for use as a heat transfer fluid, a hydraulic fluid, or for vapor phase soldering.

The fluorochemical compounds of this invention which have cyclic structures with coupled ring assemblies have lower melting and pour points than other fluorocarbon molecules with similar molecular weights, but composed entirely of open chain structures. For example, perfluorotrihexylamine ($C_{18}$) is a semi-solid at room temperature while perfluorobis(decahydronaphthalene), IIIC, Table 1, ($C_{20}$) is a liquid at room temperature. This property is important in some applications where the fluorocarbon compound must be a fluid at a given temperature. The higher boiling points of the perfluoropolycycloalkane compounds having about fifteen carbon atoms or more are suitable for higher temperature adaptations of current uses for fluorocarbon inert liquids mentioned above.

Functional coupled perfluoropolycycloalkane products containing at least one acid fluoride group can be converted to conventional derivatives such as amides, esters and alcohols or coupled further. The alcohols can be used to prepare acrylate monomers or urethane derivatives. Acrylates can be used as comonomers or crosslinking additives, e.g., for polyfunctional acrylates in the preparation of various polymers or resins. When used for this purpose these derivatives may impart water and oil resistance to the polymer or resin. Urethanes can be employed as hydrophobic additives in conformal coatings used on electronic circuit boards, or as high energy, high density binders or additives for propellants in rockets and flares.

An alternate route to the coupled perfluoropolycycloalkane compounds of this invention is by the thermal decomposition of acyl peroxide intermediates, derived from perfluorocycloalkane carbonyl fluoride precursors by reaction with sodium peroxide as disclosed in U.S. Pat. No. 3,461,155. A representative scheme for this reaction is:

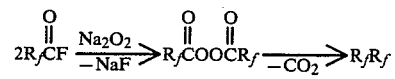

The perfluoropolycycloalkanes of this invention are, especially in the non-functional, inert form, particularly useful as fluids for use in high temperature environments, for example, as inert fluids, heat transfer fluids, and pump fluids. In the reactive, functional form, these perfluoropolycycloalkanes are useful as fluorochemical reagents, monomers, and intermediates, for example, hydroxyl group-containing compounds can be used to prepare acrylate monomers or urethane derivatives.

The following nonlimiting examples illustrate the preparation of compounds of the invention.

EXAMPLE 1

Perfluoro-3-methylcyclohexane carbonyl fluoride (IIA Table 1), (464 g, 61% —COF content) obtained from the electrochemical fluorination of m-toluyl chloride, was charged to the distillation pot of a recycle photoreactor, heated at 100° to 180° C. to distill into the reactor well, then irradiated for 24 hours, with a 450 watt medium pressure mercury lamp with continuous heating, distillation and recycling. The photoreactor contents were distilled at reduced pressure (4 to 5 torr) to yield 109 g of product boiling at 75° to 86° C. Redistillation of 62.3 g of this material at atmospheric pressure gave 55.5 g of liquid boiling between 205° to 215° C. Fluorine nuclear magnetic resonance and infrared spectral analyses of this product were consistent for the dimer IIIA of Table 1, perfluoro-3,3'-dimethylbicyclohexane. This data is summarized in Table 2.

EXAMPLES 2-6

Following the procedure of Example 1, the acid fluorides of Table 1 listed in Table 2 were converted to the coupled products of Table 1 as indicated.

TABLE 2

| Ex. No. | Acid Fluoride (Wt. % COF) | Photolysis time, (hrs.) | Product (% conv.) | Product boiling range (°C.) |
| --- | --- | --- | --- | --- |
| 1 | IIA (61) | 24 | IIIA (46) | 205–215 |
| 2 | IIB (58) | 48 | IIIB (41) | 206–289 |
| 3 | IIC (55) | 32 | IIIC (72) | 275–285 |
| 4 | IIF (47 mono, 18 di) | 32 | IIIF (48) | 275–290 |
| 5 | IIF (23 mono, 16 di) | 24 | IIIF (59) | 275–290 |
| 6 | IIE (57 mono, 16 di) | 24 | IIIE (12) | 270–285 |

EXAMPLE 7

This example describes the photocoupling of a diacid fluoride with a monoacid fluoride using a simple immersion photoreactor. A mixture of perfluorocyclohexane-1,3-dicarbonyl fluoride (IID1, Table 1), (88 g, 62% diacid fluoride content), obtained by electrochemical fluorination of isophthaloyl chloride, and perfluoro-3-methylcyclohexane carbonyl fluoride (IIA, Table 1), (177 g, 72% —COF), obtained by electrochemical fluorination of m-toluyl chloride, was irradiated with a 450 watt medium pressure mercury lamp for 24 hours. An additional 177 g of the same batch of IIA were added and photolysis was continued an additional 96 hours. The product mixture was stripped of 170 g low boiling materials (b.p. 25°–40° C.) by water aspiration (30 torr). A sample of this low boiling product was esterified with a boron trifluoride/methanol mixture to convert any residual —COF groups to —COOCH₃ and analyzed by gas liquid chromatography. The analysis revealed the presence of mainly non-functional fluorocarbon compounds, some IIA (as methyl ester) and less than 5% of IID1 (as methyl ester).

The pot residue from the water aspirator distillation was fractionated at a pressure of 4 torr to yield two fractions:
(1) 96.2 g, boiling range: 125° to 150° C., and
(2) 96.7 g, boiling range: 150° to 195° C.

A portion of fraction 2 was distilled at atmospheric pressure to yield a liquid product, 88% boiling in the range of 270° to 287° C. This product was identified by fluorine nuclear magnetic resonance and infrared spectral analyses to be mainly perfluorobis-1,3 (3'-methylcyclohexyl)cyclohexane,

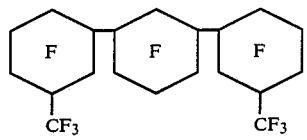

Various modifications and alterations of this invention will be apparent to those skilled in the art without departing from the scope and spirit of this invention and this invention should not be restricted to that set forth herein for illustrative purposes.

What is claimed is:

1. Fluorochemical compositions comprising carbonyl fluoride compounds in the form of perfluoropolycycloalkane ring assemblies each having (a) at least two and less than seven perfluorinated cyclohexane rings, or (b) at least two and less than seven perfluorinated decahydronaphthalene fused ring systems, or (c) combinations of at least one of said perfluorinated cyclohexane rings with at least one of said perfluorinated decahydronaphthalene fused ring systems, the sum of the perfluorinated cyclohexane rings and perfluorinated decahydronaphthalene fused ring systems being less than seven, each perfluorinated ring or ring system being directly joined to another perfluorinated ring or fused ring system by a single bond and the ring assembly having a total of at least 13 carbon atoms, said compounds having —COF ring substituents.

2. Fluorochemical compound represented by the formula

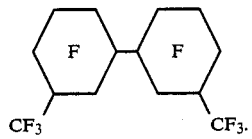

3. Fluorochemical compound represented by the formula

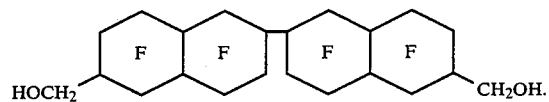

4. Fluorochemical compound represented by the formula

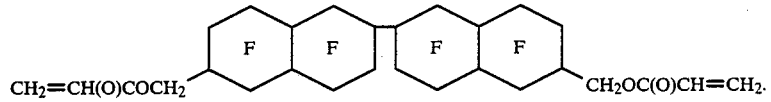

5. Fluorochemical compound represented by the formula

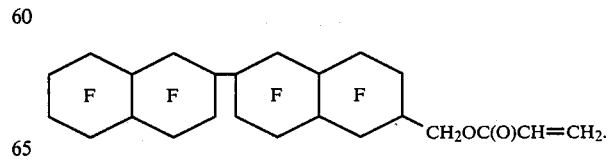

* * * * *